United States Patent [19]

Chu et al.

[11] Patent Number: 5,514,112
[45] Date of Patent: May 7, 1996

[54] DRAINAGE CATHETER AND METHOD OF USE

[75] Inventors: Michael S. H. Chu, Brookline; Daniel J. Moore, Southborough, both of Mass.

[73] Assignee: Boston Scientific Corporation, Natick, Mass.

[21] Appl. No.: 955,700

[22] Filed: Oct. 2, 1992

[51] Int. Cl.⁶ .................................................. A61M 25/00
[52] U.S. Cl. .......................... 604/267; 604/265; 604/280
[58] Field of Search ....................... 604/53, 54, 104–106, 604/164, 264, 265, 267, 268, 280

[56] References Cited

U.S. PATENT DOCUMENTS

| | | | |
|---|---|---|---|
| 3,108,595 | 10/1963 | Overment | 604/105 |
| 3,946,741 | 3/1976 | Adair | 604/105 |
| 4,182,343 | 1/1980 | Inaba | 604/268 |
| 4,249,535 | 2/1981 | Hargest, III | 604/265 X |
| 4,318,402 | 3/1982 | Vaillancourt | 604/280 |
| 4,995,868 | 2/1991 | Brazier | 604/105 |
| 5,049,138 | 9/1991 | Chevalier et al. | 604/265 |
| 5,053,009 | 10/1991 | Herzberg | 604/104 |
| 5,149,330 | 9/1992 | Brightbill | 604/280 |
| 5,193,533 | 3/1993 | Body et al. | 128/207.14 |

*Primary Examiner*—Corrine McDermott
*Attorney, Agent, or Firm*—Owen J. Meegan; Frances P. Craig

[57] ABSTRACT

A drainage catheter for draining fluids from an internal body part and a process of using the catheter wherein the catheter is subject to development of encrustations of the fluids being drained. The catheter comprises an outer flexible tubular member with a drainage lumen disposed therein. An inner flexible tubular member is slidably disposed within the outer tubular member. The inner tubular member is positioned in the outer tubular member in a predetermined location relative to the outer tubular member whereby withdrawal of the inner tubular member can cause encrustations to be broken up and removed without withdrawing the catherer from the body part being drained.

9 Claims, 2 Drawing Sheets

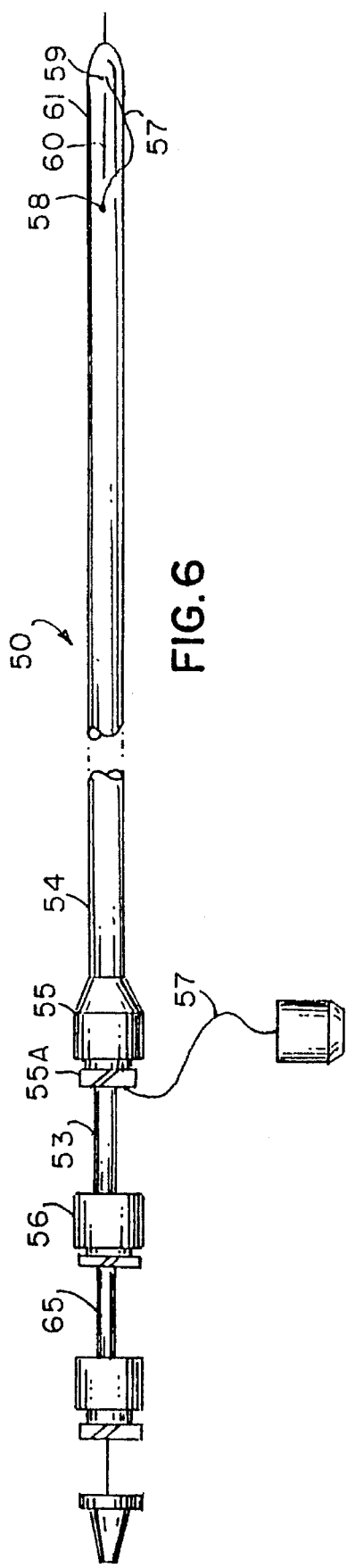
FIG.6
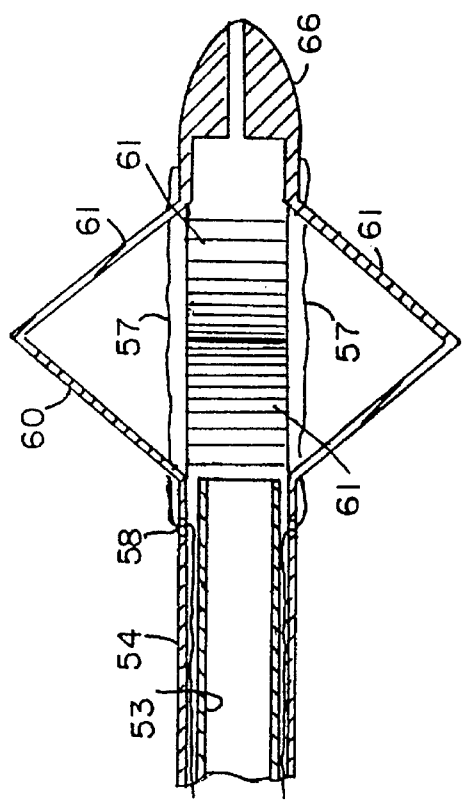
FIG.8
FIG.7

DRAINAGE CATHETER AND METHOD OF USE

BACKGROUND OF THE INVENTION

The present invention relates to a catheter that can be placed into the body for drainage of one of its parts. Parts of the body that can be drained using the present catheter include organs, abscesses, ducts, biliary and urinary tracts and cavities such as the chest or abdominal cavity. The present invention especially relates to a catheter having an outer tubular member and an inner tubular member slidably disposed in the lumen of the outer tubular member. The inner tubular member can be withdrawn from the outer tubular member to remove encrustations which form and can block the required drainage.

Most commonly, catheters of the prior art are fully removed from the body part being drained because encrustations in the lumen or at the inlet port which prevents the passage of fluids. A new catheter is then inserted in the old one's place and will remain there until it too becomes blocked or is routinely changed. Replacement of catheters not only is costly from the standpoint of service time and cost of the catheter but potentially it can be difficult procedurally because access to the part being drained can be lost during exchange procedures. An alternative approach described in the art is the use of a pusher or brush to clear the lumen. Such procedures are not commonly used because the encrustation may be pushed back into the drainage site and/or the force necessary to dislodge encrustations may result in the pusher puncturing the side of the catheter. Another procedure used to reduce encrustation is to introduce biodegradable particles and drugs into the body. Since some drugs produce allergic reactions and dosage considerations are difficult to resolve and because of a short life span such procedures have not been widely used.

SUMMARY OF THE INVENTION

According to the present invention we have found that blockages of catheter lumens due to encrustations can be eliminated with a thin walled inner tubular member that is removably disposed within an outer tubular member with the inner tubular member locked in place relative to the outer tubular member during use. When locked into place, an inlet port of the lumen of the inner tubular member is positioned in fluid flow registry with the lumen of the outer tubular member thereby enabling the inner tubular member of the catheter to be used for drainage purposes. The outer diameter of the outer tubular member is between about 1 and 8 mm. and the wall thickness is between about 0.1 and 1 mm. The outer diameter of the inner tubular member is between about 0.9 and 7 mm. and the wall thickness is between about 0.25 and 0.4 mm. The inner tubular member can thus be snugly yet slidably disposed within the lumen of the outer tubular member. When blocking encrustations occur within the lumen or at an inlet port, the inner tubular member can be unlocked and withdrawn without removing the entire catheter from the body part being drained.

The inner tubular member has a stiffness that is equal to or greater then the stiffness of the outer tubular member whereby the inner tubular member can be inserted into the outer tubular member easily and without kinking. Thus, the inner tubular member may be termed "self-supporting". In some instances, however, it may be desirable to use a relatively thin and/or limp inner tubular member and a stiffening member is disposed inside of it to provide the requisite stiffness for its insertion into the outer tubular member. In some embodiments a free board space between about 0.1 and 0.4 mm. wide is disposed between the inner tubular member and the outer tubular member. The free board space can be used as a flushing lumen by adding a side port to the proximal end of the catheter or it can be used for a suture with locking type catheters to protect the suture from encrustations. A stiffening cannula and a trocar can be disposed within the inner tubular member when the catheter is to be inserted percutaneously.

When desired, the inner tubular member can either be cleaned after withdrawal and then reinserted or the self supporting outer tubular member can be left in place without replacing the inner tubular member thereby, in either case, doubling the life of the catheter. Alternatively, a fresh inner tubular member can be inserted within the outer tubular member and the registration of the inlet ports can be reestablished. In all cases the life of the catheter can be lengthened without withdrawing it from the body part being drained. Maintenance of the catheter can even be provided while the catheter is in the body without removing it. Withdrawal of the inner tubular member can even be provided by the patients themselves without assistance thereby avoiding the procedure of insertion of a replacement catheter.

The dimensions of the inner tubular member are such that the inner tubular member is thin and flexible but stiff enough to be reinserted within the outer tubular member. Preferably the wall thickness of the inner tubular member is between about 10 and 50% of the wall thickness of the outer tubular member. In some circumstances, since the inner diameter of the inner tubular member dictates the lumen size of the inner tubular member, it may be desirable to use very thin walls. In those cases the inner tubular member can be reintroduced into the outer tubular member with a stiffening cannula which is removably disposed therein.

BRIEF DESCRIPTION OF THE DRAWINGS

FIG. 6 is a partially assembled side view of another embodiment of the present invention in which the distal end is expandable to lock it in place in the bodily part being drained.

FIGS. 7 and 8 are assembled cross sectional views of the distal end of the catheter of FIG. 6.

DESCRIPTION OF THE PREFERRED EMBODIMENTS

Figure 3:
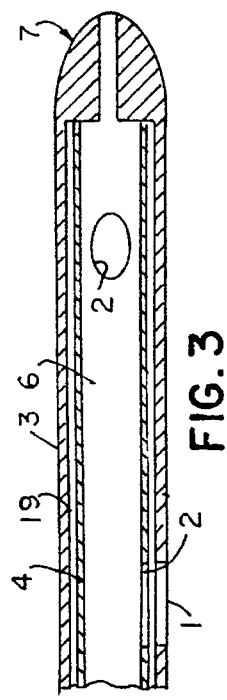
FIG. 3 is a cross sectional assembled view of another embodiment of the distal end of the drainage catheter shown in FIG. 1.

A catheter 10 according to one embodiment of the present invention is shown in FIGS. 1 to 4. The catheter 10 is formed of a flexible outer tubular member 3 and a flexible inner tubular member 4. Each of the members 3 and 4 are formed of polymeric materials conventionally used for catheters and preferably are biocompatible with and inert to bodily fluids. They optimally approach a softness of body tissue to avoid irritation of tissues when the catheter is in place. Materials having such characteristics include urethane, silicone and materials sold under the name "C-Flex" (sold by Consolidated Polymer Technologies of Largo, Fla.) and PERCU-FLEX (provided by Boston Scientific Corporation of Watertown, Mass.). The outer tubular member preferably has an outer diameter of between about 1 and 8 mm. and a wall thickness between about 0.1 and 1.0 mm. The inner tubular member 4 has an outer diameter between about 0.9 and 7.0 mm. and a wall thickness between about 0.25 and 0.4 mm. The catheter 10 is flexible and is movable in the body part in which it is inserted. It is sufficiently long, as is well known in the art, so that its distal end 7 can be disposed within the part being drained and its proximal end 8 is accessible from the outside of the patient.

The catheter of the present invention can be introduced through a bodily opening to drain an organ connected therewith or it can be introduced percutaneously. When introduced percutaneously a trocar 23 is disposed within a cannula 26 and extends through the distal end 7 of the catheter 10. The trocar 23 has a locking hub 24 disposed on the proximal end thereof. This locking hub 24 engages a cannula fitting hub 25 on a male thread 25A disposed at the proximal end. A cannula 26 is disposed within the inner tubular member 4 and is attached to the hub 25 at its end. Cannula hub 25 can be attached to inner tubular member hub 22 by means of threads 22A. Hub 22 is also used for connection of the catheter 10 to a collection bag (not shown). Inner tubular member 4 can be attached to outer tubular member 3 by means of threads 20A disposed on hub 20. Assembly of the catheter 10 is accomplished by pushing each of the members together and screwing the threaded members into the respective hubs.

Figure 2:
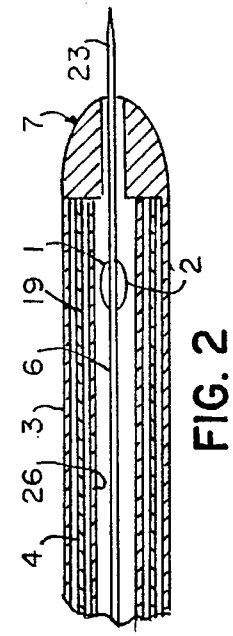
FIG. 2 is a cross sectional assembled view of an embodiment of the distal end of the drainage catheter shown in FIG. 1.

Referring to FIG. 2 the outer tubular member 3 is shown in cross-section with inlet port 1 formed in the side wall. The inner tubular member 4 is slidably disposed within the outer tubular member 3 and the distal end of inner tubular member 4 abuts the inside of tip 7. Tip 7 can be the same material used for outer tubular member 3 and can be welded in place, as is conventional in the art. Inlet port 2 formed in inner tubular member 4 is aligned with inlet port 1 so that fluids can flow into lumen 6. The embodiment shown in FIG. 2 is for percutaneous insertion of the catheter and a trocar 23 extends through the interior of the catheter to the distal end thereof and is housed within a cannula 26. After percutaneous insertion the cannula and the trocar are removed to maximize the drainage lumen.

FIG. 3 is an embodiment in which the trocar and the cannula are not in place within the catheter. The catheter of this embodiment can be inserted directly into a bodily organ through a bodily orifice or through the use of a guidewire technique. The embodiment of FIG. 3 is identical to that of FIG. 2 except that the cannula 26 and trocar 23 are not in place. The distal end 4a of the inner tubular member 4 touches the inner face 7a of the tip 7.

Registration of the inlet ports 1 and 2 in each embodiment is provided by locating the two ports relative to each other during assembly or by forming them after inserting the inner tubular member in the outer tubular member. A replacement inner tubular member can be positioned within the outer tubular member simply by withdrawing one and inserting its replacement. Since the ports 1 and 2 have to be aligned to provide for drainage, registration is provided by lining up a registration indicia 11 on the hub 22 with one on hub 20. When hub 22 is screwed onto threaded member 20A and alignment indicia 11 are in line with each other registration of the drainage ports 1 and 2 will be provided.

In some instances it may be desirable to introduce flushing liquids to the body part being drained. In those cases fluids are introduced into a free board space 19 disposed between inner tubular member 4 and the outer tubular member 3. The fluid can be conveniently introduced at the proximal end of the catheter 10 through a side port fitting on hub 22. The fluid will flow through the free board space 19 for flushing and such flushing can be continuous or intermittent as desired and the flushing fluids will emerge from the inlet port 1.

Figure 4:
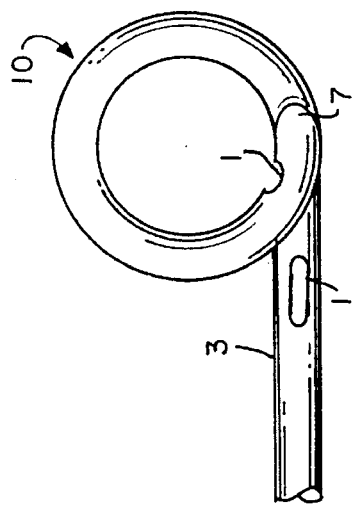
FIG. 4 is a side view of the catheter shown in FIG. 1 in which the distal end is coiled so that it can be locked in the body part being drained.

Referring to FIG. 4, the distal end of the catheter 10 is shown wrapped in a coiled shape. The outer tubular member 3 and the inner tubular member have been pre-stressed into the helical shape shown. For insertions in the body part the cannula 26 (shown in FIG. 1) is placed within the inner tubular member 4 thereby straightening the distal end of the catheter 10. When the cannula 26 is removed from the inner tubular member 4 the distal of the catheter 10 will coil into the helical shape thereby providing a mechanism for holding the catheter 10 in place during use. Removal of the catheter 10 from the bodily organ is accomplished by reinserting the cannula 26 within the catheter 10 which will straighten the distal end to enable removal and elimination of the helical shape.

Figure 5:
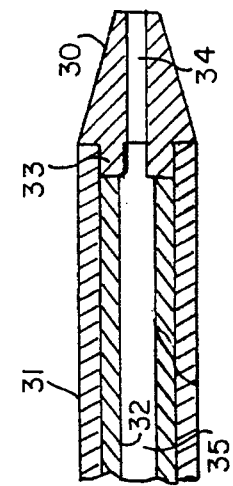
FIG. 5 is a view of an embodiment of the present invention in which the tip of the catheter is soluble in the bodily fluids it contacts after placement for drainage.
Figure 1:
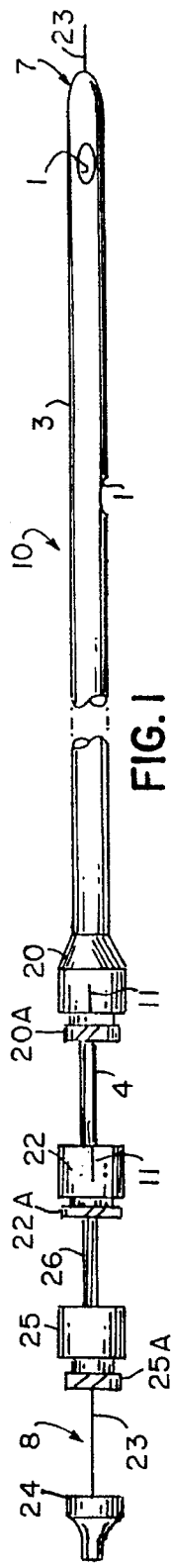
FIG. 1 is a side view of an embodiment a partially assembled drainage catheter according to the present invention.

An alternative embodiment of the tip of the catheter is shown in FIG. 5. In this embodiment, a tip 30 is inserted within the lumen of an outer tubular member 31. An inner tubular member 32 abuts a step 33 which is integrally formed on tip 30. A passageway 34 is formed within the tip 30 to allow for the flow of fluids from the body part being drained into an inner lumen 35 of the catheter and/or a trocar or guidewire, as desired.

In this embodiment the tip 30 is preferably formed of a material which is slippery when wet and soluble in bodily fluids so upon being placed within the body part to be drained it will slowly dissolve. Suitable materials are those water soluble polymers such as polyvinyl alcohol or alternatives such as polyethylene oxide, polyethylene glycol, polyacrylamides, polyvinyl pyrolidone, polyacrylic acid and the like. Such materials can be readily molded into a shape such as described herein. Preferred embodiments and alternatives of the tip are disclosed in U.S. Pat. No. to Chevalier et al, 5,049,138.

With a soluble tip 30, the inner lumen 35 of the catheter is completely open at its distal end after the tip 30 dissolves. To remove encrustations from the inner lumen, the inner tubular member 32 can be withdrawn thereby removing the encrustations together with the inner tubular member 32. Insertion of a replacement tubular member can be easily accomplished by replacing the one which is withdrawn with a new one. There is no need to replace the tip 30 which has dissolved because the catheter is already in place within the body part and is being used for drainage.

Referring now to FIG. 6 an alternative embodiment of the present invention is shown in which an expandable accordion-like lock is used to place the catheter within the bodily part being drained. The catheter 50 is similar to the embodiments of FIGS. 1 to 4 in that the catheter 50 includes an outer tubular member and an inner tubular member (53 and 54 respectively). Each of the tubular members 53 and 54 are of the same diameters as those described with reference to FIGS. 1 to 4 above. There is no need, however, for either of the inlet ports in either of the tubular members as will be discussed hereinafter.

The inner tubular member 53 is held in place within the outer tubular member 54 by means of a locking hub 55 which includes a male member 55A that can screw into a hub 56. Before screwing these members together, suture 57 is moveably disposed in the free board space between the outer tubular member and the inner tubular member. The suture 57 enters the free board space and emerges at an opening 58 and is attached to the distal end of the catheter 50 at 59. Four slits 60 are formed at right angles to each other at the distal end of the outer tubular member 54 to form segments 61. When the suture 57 is drawn in, the distal end of the outer tubular member 54 be drawn towards the proximal end thereby causing the segments between the slits to expand as shown in FIG. 8 in an accordion-like fashion.

FIG. 7 shows an embodiment in which a trocar 63 is disposed within the catheter 50 and emerges from a hole 64 in the tip. The trocar 63 is surrounded by a cannula 65 which extends the entire length of the catheter 50 and can be withdrawn as necessary after the catheter is disposed within the body part being drained. The catheter 50, however, does not have to have the trocar 63 to be inserted in many bodily organs through bodily cavities. A guidewire can be substituted for the trocar, as is conventional.

As shown in FIG. 8 the suture 57 is drawn back (and locked between threaded member 55A and hub 56) the suture 57 draws the distal end 66 of the catheter 50 and causes the segments 61 of the catheter between tip to be drawn back and bent outwardly. The spaces between the segments 61 become ports for the flow of fluids being drained and the outwardly bent segments will anchor the catheter in place within the body part. In the embodiment shown, four slits are made in the distal end of the catheter and thus four segments will be made between them.

To withdraw the catheter entirely from the organ being drained, a cannula is inserted within the inner tubular member until it abuts the interior of the distal end of the catheter thereby straightening out the segments 61 for easy withdrawal. On the other hand, prior to withdrawal of the entire catheter, the inner tubular member 53 can be withdrawn from the catheter simply by withdrawing it and if another tubular member is to be inserted then this replacement can be inserted as was described with reference to FIG. 1 (with no need for alignment, however).

In use, referring to FIGS. 1 to 4, the catheter 10 is inserted into a bodily organ (not shown) in the usual way. When inserted, the bodily fluids will pass through the inlet ports 1 and 2 and into the inner lumen 6 and ultimately into a collection bag. At either a predetermined time, or when the fluids stop flowing, the hub 22 is unscrewed from the hub 20 and the inner tubular member 4 is withdrawn from the outer tubular member 3. A new inner tubular member 4 can then be inserted within the outer tubular member 3. The indicia 11 are aligned with each other and thus the inlet ports 1 and 2 are in alignment with each other at the distal end of the catheter 10. Alternatively, the outer tubular member 3, alone, can be used to collect bodily fluids that are to be drained and a replacement inner tubular member 4 need not be inserted into place. This may be important when the catheter will be removed shortly from the bodily organ. In any event, there is no need to replace the entire catheter when using the herein described invention.

If encrustations are located in the inlet ports 1 and/or 2, withdrawal of the inner tubular member 4 will break them up and the bodily fluid flow can resume through the outer tubular member 3. The serviceable life of the catheter 10 in place in the organ can thus be effectively doubled because the lumen of the inner outer tubular member serves for the transfer as well as a housing for the inner tubular member 4.

It is apparent that modifications and changes can be made within the spirit and scope of the present invention but it is our intention, however, only to be limited by the scope of the appended claims.

As our invention we claim:

1. A drainage catheter formed of tubular members with proximal and distal ends for draining fluids from an internal body part, said catheter being subject to development of encrustations from the fluids being drained, said catheter comprising:

a flexible outer tubular member having a drainage lumen disposed therein, said outer member having an inlet end and an outlet end;

a flexible inner tubular member slidably and removably disposed within said outer tubular member, said inner tubular member having a drainage lumen disposed therein, said inner tubular member having an outlet end;

an inlet port at the distal end of each of said inner and outer tubular members to allow for the drainage of fluids from said body part into said catheter, wherein the inlet ports are apertures on the side walls of the distal end of each of said inner and said outer tubular members;

means to position said inner tubular member in a predetermined location relative to said outer tubular member whereby the respective inlet ports can be positioned to drain fluids, wherein said means to position said inner tubular member may be used to position said apertures in registry with each other to drain fluids; and means to withdraw entirely said inner tubular member from said outer tubular member whereby encrustations in said catheter can be broken up and removed without removing the entire catheter from the body part being drained;

wherein said outer tubular member is sufficiently self-supporting to allow for drainage of fluids from said body part through said outer member drainage lumen after withdrawal of said inner member from said outer member, and wherein said inner tubular member is sufficiently self-supporting to allow for reinsertion of said inner member easily and without kinking into said outer member while said outer member remains inserted in said body part.

2. The drainage catheter according to claim 1 further including an abutment disposed at the distal end of said inner tubular member and an abutment within the distal end of said outer tubular member, said abutments defining the distance between the end of the outer tubular member and the aperture on said outer tubular member whereby the aperture of said inner tubular member can be registered with the aperture on said outer tubular member.

3. The drainage catheter according to claim 1 wherein the outside of the inner tubular member closely engages the lumen of the outer tubular member.

4. A drainage catheter formed of tubular members with proximal and distal ends for draining fluids from an internal body part, said catheter being subject to development of encrustations from the fluids being drained, said catheter comprising:

a flexible outer tubular member having a drainage lumen disposed therein, said outer member having an inlet end and an outlet end;

a flexible inner tubular member slidably and removably disposed within said outer tubular member, said inner tubular member having a drainage lumen disposed therein, said inner tubular member having an outlet end;

an inlet port at the distal end of each of said inner and outer tubular members to allow for the drainage of fluids from said body part into said catheter;

means to position said inner tubular member in a predetermined location relative to said outer tubular member whereby the respective inlet ports can be positioned to drain fluids; means to withdraw entirely said inner tubular member from said outer tubular member whereby encrustations in said catheter can be broken up and removed without removing the entire catheter from the body part being drained;

wherein said outer tubular member is sufficiently self-supporting to allow for drainage of fluids from said body part through said outer member drainage lumen after withdrawal of said inner member from said outer member, wherein said inner tubular member is sufficiently, self-supporting to allow for reinsertion of said inner member easily and without kinking into said outer member while said outer member remains inserted in said body part, and wherein a soluble tip is disposed on the distal end of said outer tubular member, said tip having a step disposed thereon, said step being arranged to snugly fit within the outer tubular member.

5. The drainage catheter according to claim 4 wherein the outside of the inner tubular member closely engages the lumen of the outer tubular member.

6. A process using a drainage catheter, said process comprising:

introducing a flexible catheter into a body part, said catheter having a inner tubular member with an internal lumen therein, said inner tubular member being slidably and removably disposed within an internal lumen of a outer tubular member, said tubular members having inlet ports on the distal ends of each of the members;

placing said ports in registry with each other whereby to allow the flow of bodily fluids from the body part through said ports and into a lumen within the inner tubular member; and periodically entirely withdrawing only the inner tubular member from the outer tubular member and allowing the outer tubular member to remain in place in said body part whereby encrustations in said catheter can be broken up and removed without removing the catheter from the body part being drained;

after withdrawal of said inner member from said outer member, continuing drainage of fluids from said body part through said outer member drainage lumen while said outer member remains inserted in said body part, said outer tubular member being sufficiently self-supporting to allow for such drainage.

7. The process according to claim 6 wherein the outer diameter of said outer tubular member is between about 1 and 8 mm. and the wall thickness is between about 0.1 and 1 mm. and wherein the outer diameter of said inner tubular member is between about 0.9 and 7 mm. and the wall thickness is between about 0.25 and 0.4 mm whereby said inner tubular member is snugly but slidably disposed within the outer tubular member.

8. The process according to claim 6 further comprising the steps of introducing either the inner tubular member that was withdrawn or a new inner tubular member into said outer tubular member after said inner tubular member has been withdrawn for removal of encrustations said inner tubular member being sufficiently self-supporting to allow for introduction of said inner member easily and without kinking while said outer member remains inserted in said body part; and further placing said ports in registry with each other.

9. The process according to claim 8 wherein said ports are on the sidewalls of the inner tubular member and the outer tubular member.

\* \* \* \* \*